United States Patent
McCall, Jr.

(10) Patent No.: US 7,816,404 B2
(45) Date of Patent: Oct. 19, 2010

(54) METHODS FOR THE PREPARATION AND USE OF FERRIC PYROPHOSPHATE CITRATE CHELATE COMPOSITIONS

(75) Inventor: William S. McCall, Jr., Raleigh, NC (US)

(73) Assignee: Rockwell Medical Technologies, Inc., Wixom, MI (US)

( * ) Notice: Subject to any disclaimer, the term of this patent is extended or adjusted under 35 U.S.C. 154(b) by 309 days.

(21) Appl. No.: 12/138,018

(22) Filed: Jun. 12, 2008

(65) Prior Publication Data

US 2009/0023686 A1    Jan. 22, 2009

Related U.S. Application Data

(60) Provisional application No. 60/961,327, filed on Jul. 20, 2007.

(51) Int. Cl.
*A61K 31/295* (2006.01)
*A61K 33/26* (2006.01)

(52) U.S. Cl. .................. 514/502; 424/646
(58) Field of Classification Search ........... 514/502; 424/646
See application file for complete search history.

(56) References Cited

U.S. PATENT DOCUMENTS

| | | |
|---|---|---|
| 3,027,303 A | 3/1962 | Wolcott |
| 3,259,500 A | 7/1966 | Barnhart et al. |
| 3,275,514 A | 9/1966 | Saltman et al. |
| 3,367,834 A | 2/1968 | Dexter et al. |
| 3,686,397 A | 8/1972 | Muller |
| 3,886,267 A | 5/1975 | Dahlberg et al. |
| 4,058,621 A | 11/1977 | Hill |
| 4,167,564 A | 9/1979 | Jensen |
| 4,834,983 A | 5/1989 | Hider et al. |
| 5,063,205 A | 11/1991 | Peters et al. |
| 5,177,068 A | 1/1993 | Callingham et al. |
| 2003/0190355 A1 | 10/2003 | Hermelin et al. |
| 2006/0134227 A1 | 6/2006 | Bortz et al. |

FOREIGN PATENT DOCUMENTS

| | | |
|---|---|---|
| WO | WO 95/22908 | 8/1995 |
| WO | WO 01/00204 | 1/2001 |

OTHER PUBLICATIONS

Moody, Mark D. et al., "Iron Transport and Its Relation to Heme Biosynthesis in Rhodopseudomonas sphaeroldes," Journal of Bacteriology, vol. 161, Mar. 1985, pp. 1074-1079.
Caspari, Jr., Charles, "A Treatise on Pharmacy for Students and Pharmacists," Lea Brothers & Co., 1906, pp. 556-557.

*Primary Examiner*—Porfirio Nazario Gonzalez
(74) *Attorney, Agent, or Firm*—Price, Heneveld, Cooper, DeWitt & Litton, LLP

(57) ABSTRACT

A highly water soluble ferric pyrophosphate citrate chelate useful for treating iron deficiency contains 2% or less phosphate by weight. These chelate compositions are easily milled and/or processed into dosage forms using conventional techniques, and are expected to exhibit advantageous biocompatibility as compared to conventional soluble ferric pyrophosphates, ferric salts, ferric polysaccharide complexes and ferrous salts.

23 Claims, No Drawings

METHODS FOR THE PREPARATION AND USE OF FERRIC PYROPHOSPHATE CITRATE CHELATE COMPOSITIONS

CROSS REFERENCE TO RELATED APPLICATION

This application claims priority under 35 U.S.C. §119(e) on U.S. Provisional Application No. 60/961,327 entitled METHODS FOR THE PREPARATION AND USE OF FERRIC PYROPHOSPHATE CITRATE CHELATE COMPOSITIONS, filed Jul. 20, 2007, by William S. McCall, the entire disclosure of which is incorporated herein by reference.

BACKGROUND OF THE INVENTION

Iron deficiency is the most common micronutrient deficiency in the world, affecting 1.3 billion people (i.e., 24% of the world's population). Severe iron deficiency, i.e., iron deficiency anemia, is particularly debilitating, since iron has several vital physiological functions, including: (1) carrier of oxygen from lung to tissues; (2) transport of electrons within cells; and (3) co-factor of essential enzymatic reactions in neurotransmission, synthesis of steroid hormones, synthesis of bile salts, and detoxification processes in the liver. Among the consequences of iron deficiency anemia are increased maternal and fetal mortality, an increased risk of premature delivery and low birth weight, learning disabilities and delayed psychomotor development, reduced work capacity, impaired immunity (high risk of infection), an inability to maintain body temperature, and an associated risk of lead poisoning because of pica.

Iron deficiency anemia commonly affects patients having chronic diseases, such as kidney disease, inflammatory bowel disease, cancer, HIV, and diabetes. For example, patients receiving regular dialysis treatments for chronic renal failure very frequently are also afflicted with anemia. It is believed that prior to the availability of recombinant erythropoietin, a recombinant DNA version of the human erythropoietin protein that simulates the production of red blood cells, as many as about 90 percent of all kidney dialysis patients experienced debilitating anemia. A primary cause of anemia in dialysis patients is the inability of the kidneys to produce sufficient erythropoietin to generate adequate amounts of red blood cells. Although erythropoietin therapy simulates red blood cell production and is very often effective at reducing or eliminating anemia, iron deficiencies are also common among dialysis patients and can result in anemia despite erythropoietin therapy. Accordingly, in addition to erythropoietin therapy, it will often be necessary and desirable to deliver iron in a biologically available form to the blood of anemic dialysis patients in order to effectively treat the anemia. Further, there is evidence that iron supplementation can reduce the dose of erythropoietin needed to effectively treat anemia, even for patients that do not have an iron deficiency. This can be very important because recombinant erythropoietin is an expensive drug and can cause mild hypertension and flu-like symptoms. Therefore, it is often desirable to augment erythropoietin therapy with effective iron supplementation.

It is well known to treat an iron deficiency with orally administered iron supplements. Conventional oral iron fortificants can be divided into 4 groups: (1) freely water soluble (e.g., ferrous sulphate, ferrous gluconate, ferrous lactate and ferric ammonium citrate); (2) poorly water soluble (e.g., ferrous fumarate, ferrous succinate, and ferrous saccharate); (3) water insoluble (e.g., ferric pyrophosphate, ferric orthophosphate, and elemental iron); and (4) experimental [e.g., sodium-iron EDTA and iron-porphyrin (heme) complexes isolated from bovine hemoglobin].

In general, relatively large doses of oral iron fortificants are needed to achieve a desired therapeutic effect. The absorption of non-heme iron from the gastrointestinal tract varies from 2% to greater than 90% because it is strongly influenced by the iron status of the body, the solubility of the iron salts, the integrity of gut mucosa, and the presence of absorption inhibitors or facilitators in ingesta. For example, foods which contain polyphenol compounds and/or phytic acid bind with dietary iron, decreasing the concentration of free iron in the gut and forming complexes that are not absorbed. Cereals such as wheat, rice, maize, barley, sorghum and oats; vegetables such as spinach and spices; legumes such as soya beans, black beans, and peas; and beverages such as tea, coffee, cocoa and wine contain substances that inhibit iron absorption from the gut. L-Ascorbate and L-cysteine are known to facilitate absorption of iron.

Oral administration of iron supplements is known to be commonly accompanied by undesirable side effects, including nausea, vomiting, constipation and gastric irritation. For these and other reasons, patient noncompliance is also a common problem.

To overcome the above-described problems with oral delivery of iron, a great deal of effort has been directed to developing iron-containing formulations that are suitable for parenteral administration. Parenterally administered formulations are, in general, aqueous solutions of specific formulation components, in which the solution pH is in the range from about pH 4 to about pH 8. Parenteral administration encompasses administration by intravenous injection, intramuscular injection, or dialysis.

The formulation of iron-containing compositions for parenteral administration is particularly difficult. The solubility of iron compounds in water is strongly dependent on the pH of the solution and the presence of other formulation components. In general, iron salts are soluble in acidic solutions. Conversely, in basic solutions, unless a chelating agent, such as EDTA, is present, iron ions will form insoluble oxides and precipitate from the formulation.

In addition, formulation of iron compounds in aqueous solutions presents added degrees of difficulty related to the redox chemistries of iron and its ability to catalyze oxidation reactions. With respect to redox chemistries, iron has two common oxidation states, the ferrous or $Fe^{+2}$ state and the ferric or $Fe^{+3}$ state. In general, iron compounds in which iron is in its ferrous oxidation state are more soluble in water than are iron compounds in which iron is in its ferric oxidation state. In the presence of reducing agents, such as L-ascorbate or L-cysteine, iron is known to cycle from its ferric to its ferrous oxidation state and vice versa. Iron ions in solution are highly reactive oxidizing agents and catalysts for oxidation of other formulation components. For example, iron ions in solution are known to catalyze oxidation of dextrose, polysaccharides, amines, and phenols to cause formation of degradation products having undesirable properties, such as color, biological activities, and toxicities that are different from those of the unoxidized substances.

With respect to intravenous administration, iron dextran (INFED®), which may be obtained from Watson Pharmaceuticals, Corona, Calif., is formulated in water containing 0.9% (by weight) sodium chloride for parenteral administration. [Physicians Desk Reference, 59th edition, 2005, pages 3301-3303]. Iron dextran is a dextran macromolecule having a molecular weight ranging generally between about 100,000 and about 200,000 to which iron is bound by both ionic bonds and weak electrostatic interactions. Iron dextran thus formulated occasionally causes severe allergic reactions, fever and rashes during injection. Parenteral administration intramuscularly is painful and often results in an undesirable discoloration at the injection site. Further, only about half of the iron in iron-dextran is bioavailable after intravenous injection. The fate of the rest is unknown.

Intravenous administration of iron saccharide complexes such as iron dextran requires venous access and the commercially available intravenously administered iron supplements, such as iron dextran and ferric gluconate, are relatively expensive and require a great deal of time and skill to administer.

Intraperitoneal delivery of iron dextran has been used to treat anemia. However, there is evidence that iron dextran, when administered intraperitoneally, is stored in macrophages near the peritoneum and could create abnormal changes in the peritoneum.

Other iron preparations which may be administered by injection are taught in U.S. Pat. No. 5,177,068 to Callingham et al., U.S. Pat. No. 5,063,205 to Peters and Raja, U.S. Pat. No. 4,834,983 to Hider et al., U.S. Pat. No. 4,167,564 to Jenson, U.S. Pat. No. 4,058,621 to Hill, U.S. Pat. No. 3,886,267 to Dahlberg et al., U.S. Pat. No. 3,686,397 to Muller, U.S. Pat. No. 3,367,834 to Dexter and Rubin, and U.S. Pat. No. 3,275,514 to Saltman et al., for example. In general, these are formulations of iron bound to polymeric substrates, or chelated by various ligands, saccharides, dextrans, hydrolyzed protein, etc. All have been unsuccessful and/or possess such severe adverse side effects that practical utilization has not occurred.

It is known to deliver iron to an iron-deficient patient via dialysis using a composition comprising an ionic iron complex. An advantage is that the dialysis treatment delivers iron to the blood at a relatively constant rate throughout the dialysis session. This is because there is negligible free iron in plasma since iron rapidly binds with transferrin.

Soluble ferric pyrophosphate (alternatively, "ferric pyrophosphate, soluble") is an iron preparation of uncertain composition. No definite formula for its constitution is known. In general, it is described as "a mixture of ferric pyrophosphate and sodium citrate" or "a mixture of four salts (ferric and sodium pyrophosphates and ferric and sodium citrates)" or "ferric pyrophosphate that has been rendered soluble by sodium citrate." Soluble ferric pyrophosphate is known to have the properties described in Table 1.

TABLE 1

Properties of Conventional Ferric Pyrophosphate, Soluble

| Parameter | Observation |
|---|---|
| Chemical Name | 1,2,3-Propanetricarboxylic acid, 2-hydroxy-, iron(3+) sodium salt (1:1:1), mixture with iron(3+) diphosphate |
| CAS Registry No. | 1332-96-3 |
| Appearance | Solid (may be plates, powder, or pearls, depending on the manufacturer) |
| Color | Yellow-green to apple-green |
| Iron content | 10.5% to 12.5% |
| Solubility in water | Exceeds 1 g per mL |
| pH of a 5% solution | 5-7 |

Soluble ferric pyrophosphate may be obtained commercially. Conventional soluble ferric pyrophosphate is an apple-green solid containing from about 10.5% to about 12.5% iron. According to the manufacturers, soluble ferric pyrophosphate is stable for as long as three years provided that it is protected against exposure to air and light. Analysis of conventional soluble ferric pyrophosphates has shown that typical conventional preparations contain iron, pyrophosphate anion, citrate anion, phosphate anion, sulfate anion, and sodium (Table 2).

TABLE 2

Composition of conventional soluble ferric pyrophosphates

| | Weight Percent Composition on the Dried Basis | | | | | |
|---|---|---|---|---|---|---|
| Sample No. | A | B | C | D | E | F |
| Iron | 11.8 | 11.4 | 11.9 | 11.1 | 12.0 | 12.0 |
| Pyrophosphate | 10.1 | 8.3 | 4.7 | 9.1 | 9.2 | 10.1 |
| Citrate | 34.3 | 35.9 | 44.2 | 37.6 | 35.8 | 36.5 |
| Phosphate | 16.8 | 17.1 | 12.9 | 15.8 | 17.4 | 16.3 |
| Sodium | 16.0 | 16.1 | 16.6 | 16.2 | 16.4 | 16.2 |
| Sulfate | 12.6 | 16.4 | 15.9 | 19.5 | 14.6 | 4.2 |

Methods for the preparation of the mixture known as soluble ferric pyrophosphate are provided by Caspari. (Charles Caspari, "Treatise on Pharmacy for Students & Pharmacists, Lea Brothers & Co., 1906, pages 556-557.) A preparation disclosed by Caspari is made by precipitating a white ferric pyrophosphate, $Fe_4(P_2O_7)_3$, from a solution of ferric sulphate by means of sodium pyrophosphate, dissolving this precipitate in a solution of sodium or ammonium citrate and concentrating and scaling the solution so obtained. In the alternative, Caspari wrote that this iron preparation is made by adding 11 parts of crystallized sodium pyrophosphate to a solution of 11 parts of ferric citrate in twice its weight of water, evaporating the resulting green-colored solution at a temperature not exceeding 60° C. (140° F.) to obtain a syrupy consistency, and spreading the syrupy material on glass plates to allow solidification. Although modern processing techniques have likely been applied to the latter method of preparation, the process suffers from a number of serious drawbacks, including the fact that ferric citrate, a key starting material, is an unstable substance of unknown composition; the consistency and viscosity of a "syrupy" composition is undefined; and the means for isolating and purifying the product are not disclosed. Irrespective of the conventional method of preparation, examination of Table 2 clearly shows that the anion composition of conventional soluble ferric pyrophosphate is widely variable, with a pyrophosphate content ranging from about 4.7% to about 10.1%; a citrate content ranging from about 34.3% to about 44.2%; a phosphate content ranging from about 12.9% to about 17.4%; and a sulfate content ranging from about 4.2% to about 19.5%.

SUMMARY OF THE INVENTION

The present invention provides water-soluble iron chelate compositions comprising ferric pyrophosphate citrate chelate compositions. A chelate composition of the invention comprises pyrophosphate and citrate chelated to ferric iron. Chelate compositions of the invention are water-soluble iron fortificants and are useful for the treatment of iron deficiency anemia, particularly the anemia of chronic disease.

These and other features, advantages and objects of the present invention will be further understood and appreciated by those skilled in the art by reference to the following specification and claims.

DETAILED DESCRIPTION OF THE INVENTION

Compositions in accordance with certain aspects of the invention comprise stable, water-soluble ferric pyrophosphate citrate chelate compositions, having, by weight, from about 7% to about 11% iron, from about 14% to about 30% citrate, from about 10% to about 20% pyrophosphate and about 2% or less phosphate. The chelate compositions may have, by weight, about 1.5% phosphate or less, or about 1% phosphate or less. In an aspect of the invention, the chelate compositions have, by weight, about 0.1% phosphate or less. Sulfate ion content is typically from about 20% to about 35% by weight.

Methods in accordance with certain aspects of the invention comprise steps for the preparation of stable, water-soluble ferric pyrophosphate citrate chelate compositions, having, by weight, from about 7% to about 11% iron, from about 14% to about 30% citrate, from about 10% to about 20% pyrophosphate and about 2% or less phosphate. The chelate compositions may have, by weight, about 1.5% phosphate or less, or about 1% phosphate or less. In an aspect of the invention, the chelae compositions have, by weight, about 0.1% phosphate or less. Sulfate ion content is typically from about 20% to about 35% by weight.

In certain aspects of the invention, water-soluble ferric pyrophosphate citrate chelate compositions are used as a food additive, nutritional supplement, dietary supplement, medical food, nutrient, iron fortificant, and source of iron in the fields of nutrition for humans, animals, fish, and birds and diagnostics. Soluble ferric pyrophosphate citrate chelate compositions are used as a pharmaceutical and pharmacologically active ingredient for human clinical and veterinary applications in certain aspects of the invention.

A method of administering a water-soluble ferric pyrophosphate citrate chelate composition to a subject in need of such administration for the prevention or treatment of iron deficiency or anemia is provided in certain aspects of the invention.

According to a method of the present invention, a water-soluble ferric pyrophosphate citrate chelate composition is administered, alone or in combination with other substances (e.g., along with materials necessary to form a tablet, caplet, pill, capsule, troche, lozenge, powder, granulate, or solution that is suitable for ingestion) in sufficient quantities to prevent the onset or reverse the course of deleterious effects brought about by iron deficiency. Further, according to a method of the present invention, a water-soluble ferric pyrophosphate citrate chelate composition of the invention is administered, alone or in combination with other substances, in sufficient quantities in a formulation for parenteral administration to prevent the onset or reverse the course of deleterious effects brought about by iron deficiency.

A method of the present invention employs a composition as described hereinabove, which is administered to a mammal by oral ingestion or injection. The composition, so administered, may be regarded either as a food additive, a substance that is generally regarded as safe (i.e., a GRAS substance), or a drug within the meaning of Title 21 of the Code of Federal Regulations (CFR).

In a method of the present invention, a chelate composition as described hereinabove may be ingested as a food supplement, dietary supplement, nutritive supplement, or medical food. The terms "food supplement, dietary supplement, and nutritive supplement" encompass or include a composition of the present invention that augments the iron that is present in food, components of the diet, and compositions intended to provide nutrition. The term "medical food" encompasses or includes a chelate composition of the present invention that is prescribed by a clinician or physician for the purpose of augmenting iron in ingesta.

In a method of the invention, a chelate composition as described herein may be administered as a drug either orally or by injection.

Included within the scope of this invention is a method of treating iron deficits in a warm-blooded animal, including a human, using pharmaceutical compositions comprising a soluble ferric pyrophosphate citrate chelate composition of the invention and a suitable pharmaceutical carrier. For the purpose of this disclosure, a warm-blooded animal is a member of the animal kingdom which includes but is not limited to mammals and birds.

The term "chelate" as used herein generally means a metal cation and anions that surround the metal cation and are joined to it by electrostatic bonds. A water-soluble ferric pyrophosphate citrate chelate composition of the invention comprises a ferric iron cation surrounded by and joined by electrostatic bonds to both citrate and pyrophosphate anions.

The term "excipient material" means any compound forming a part of the formulation which is not intended to have biological activity itself and which is added to a formulation to provide specific characteristics to the dosage form, including by way of example, providing protection to the active ingredient from chemical degradation, facilitating release of a tablet or caplet from equipment in which it is formed, and so forth.

The terms "treating" and "treatment" and the like are used herein to generally mean obtaining a desired pharmacological and physiological effect. The effect may be palliative, prophylactic in terms of preventing or partially preventing a disease, symptom or condition thereof, and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; (c) relieving the disease, causing regression of the disease and/or its symptoms or conditions; or (d) returning a clinical value to the concentration range normally found in a subject.

The phrase "therapeutically effective" is intended to qualify the amount of an active agent needed in an orally or parenterally administered therapy which will achieve the goal of abating, mitigating, reducing or preventing, for example, an iron deficiency disorder, or of restoring physiologically adequate concentrations of iron while avoiding adverse side effects typically associated with conventional iron compositions.

The term "suitable for intravenous injection" as used herein has its conventional meaning as understood by skilled artisans when referring to a composition that meets the general requirements for solutions for injection as presented in the General Chapter of the U.S. Pharmacopoeia entitled "Injections." (U.S. Pharmacopoeia, U.S. Pharmacopoeial Convention, Inc., Rockville, Md., 2006.)

The term "parenteral nutrition composition" means a composition for parenteral administration.

The term "dialysis therapy" means the clinical treatment of chronic kidney disease comprising the osmotic exchange of metabolites, toxins and water across a membrane from a renal disease patient's blood to a dialysate solution. Conventional dialysis therapy is described by S. Pastan and J. Bailey in the article entitled "Dialysis therapy" published in The New England Journal of Medicine, volume 338, number 20, pages 1428-1437 (1998).

The term "dialysate" means a composition for intravenous administration as part of a dialysis procedure for the treatment of chronic kidney disease. Dialysate is conventionally provided for use in either peritoneal dialysis (in which the peritoneal membrane constitutes the dialysis membrane) or hemodialysis (in which a synthetic membrane constitutes the dialysis membrane). Hemodialysate is generally prepared from two dry powder concentrates, including acid ("A") and base ("B") concentrates, which are reconstituted in treated water before use, or from two aqueous concentrates. The A concentrate, containing an organic acid and electrolytes and osmotic agents other than bicarbonate, is mixed with B concentrate containing bicarbonate and treated water in a dialysis machine to make the final hemodialysate. Peritoneal dialysate is a premixed solution of osmotic agents, electrolytes, and water that is used in dialysis without further constitution.

After diligent and lengthy experimentation, the inventor has discovered water-soluble ferric pyrophosphate citrate chelate compositions comprising about 2% or less phosphate. The chelate compositions may have, by weight, about 1.5% phosphate or less, or about 1% phosphate or less. In certain aspects, the chelate compositions have, by weight, about 0.1% phosphate or less.

The methods for the preparation of the water-soluble ferric pyrophosphate citrate chelate compositions of the present invention comprise combining citrate and pyrophosphate ions in water, adding ferric ion, and isolating water-soluble ferric pyrophosphate citrate chelate compositions therefrom. The following parameters may affect product yield, quality and/or composition: (a) the ratio of iron to citrate to pyrophosphate; (b) the purity of each raw material; (c) the volume of water that is employed; (d) the reaction temperature; (e) the organic solvent that is used to cause precipitation of the desired product, a ferric pyrophosphate citrate chelate composition of the invention; (f) the volume of organic solvent that is used to cause precipitation; and (g) the drying temperature.

A molar ratio of $Fe^{3+}$ to citrate to pyrophosphate of about 1:1:0.5 may be used for obtaining a composition of the present invention. Variations in this ratio of about ±10% are tolerable, i.e., the molar ratio of $Fe^{3+}$ to citrate to pyrophosphate may be 0.9 to 1.1 moles $Fe^{3+}$:0.9 to 1.1 moles citrate: 0.45 to 0.55 moles pyrophosphate. Larger changes in the molar ratio result in compositions that are different from those of the present invention. For example, use of a molar ratio of 1:0.5:1 ($Fe^{3+}$ to citrate to pyrophosphate) fails to provide a chelate composition.

Each raw material exhibits high purity. The ferric salt, citrate, and pyrophosphate starting materials each contain less than 250 micrograms of the metals aluminum, antimony, arsenic, bismuth, cadmium, copper, lead, mercury, molybdenum, thallium, and tin per gram of the starting material, since these metals exhibit known toxicities in humans. The pyrophosphate preferably contains less than about 0.1% phosphate, and more preferably less than about 0.01% phosphate.

A volume of water equal to 2 milliliters (±10%) of water for each gram of ferric salt starting material is adequate for dissolution of all the starting materials and the resulting chelate composition product and enables precipitation of the desired chelate composition by the addition of an organic solvent. If substantially smaller volumes of water are used, the starting materials may not dissolve completely. If substantially larger volumes of water are used, the desired chelate composition may not precipitate or may precipitate in low yield after addition of an organic solvent. Typically, a volume of water of from about 1.5 milliliters to about 10 milliliters for each gram of ferric salt can be used for dissolution of the starting materials.

Before addition of the ferric salt starting material, the reaction temperature may be increased to a temperature in the range from about 70° C. to about 85° C. in order to achieve complete dissolution of the starting materials. Once dissolution is complete, the reaction temperature may be lowered to a temperature in the range from about 15° C. to about 75° C. to prevent hydrolysis of pyrophosphate to phosphate in the presence of ferric ion, preferably from about 15° C. to about 39° C.

The inventor has discovered that organic solvents such as methanol, ethanol, propanol, 2-propanol, acetonitrile, acetone, and 2-butanone are useful in precipitating the desired chelate composition.

A volume of 14 milliliters (±10%) of methanol for each gram of ferric salt starting material may be used. The addition of substantially smaller volumes may result in incomplete precipitation of the desired chelate composition. The addition of larger volumes could increase the risk of contamination with unwanted by-products. Suitable amounts of methanol and/or other organic solvents may range from about 10 to about 25 milliliters per gram of ferric ion source.

If a wet cake of the desired chelate composition (i.e., a mass of the product that contains water and methanol) is dried at a temperature that exceeds about 80° C., pyrophosphate is hydrolyzed to phosphate. Thus, it is preferred that the precipitate is dried at a temperature of 80° C. or less.

While not wishing to be bound by any particular hypothesis or theory, the inventor expects that the soluble ferric pyrophosphate citrate chelate compositions of the invention afford the significant advantages that (a) the ferric iron is strongly chelated by both pyrophosphate and citrate; and (b) the chelate composition is very water-soluble.

The strength of the electrostatic bond between a ligand and a metal ion is conventionally described by a stability constant, $K_{stab}$, and frequently expressed as the logarithm of that constant. [Martell A E, Smith R M. Critical Stability Constants. Volumes 1-6. New York: Plenum Press; 1974, 1975, 1976, 1977, 1982, and 1989.] The log $K_{stab}$ for ferric ion with citrate is 12 and the log $K_{stab}$ for ferric ion with pyrophosphate is 22.2. [Gupta A J, Crumbliss A L. Treatment of iron compounds suitable for parenteral administration? J Lab Clin Med 2000; 136: 371-178.] These stability constants are several orders of magnitude greater than the stability constants for ferric ion with other anions such as chloride or gluconate, indicating that the electrostatic bonds between ferric ion and citrate and between ferric ion and pyrophosphate are stronger than the bonds to other ligands. Chelate compositions of the present invention have a solubility in water that exceeds 1 gram per milliliter. Chelate compositions of the present invention contain, by weight, from about 10% to about 20% pyrophosphate. Recent studies have shown that polyphosphate compounds are possible candidates for intracellular iron transport, and among these polyphosphate compounds, pyrophosphate has been shown to be the most effective agent in triggering iron exchange with transferrin. [Konopka K, Mareschal J C, Crichton R R. Iron transfer from transferrin to ferritin mediated by pyrophosphate. Biochem Biophys Res Commun 1980; 96(3):1408-13. Pollack S, Vanderhoff G, Lasky F. Iron removal from transferrin. An experimental study. Biochim Biophys Acta 1977; 497(2):481-7. Muralidhara B K, Hirose M. Anion-mediated iron release from transferrins. The kinetic and mechanistic model for N-lobe of ovotransferrin. J Biol Chem 2000; 275(17):12463-9.] The structure of the ferric pyrophosphate citrate chelate of the invention resembles the putative structure of the pyrophosphate enzyme complex that enables iron transfer to transferrin. [Cowart R E, Swope S, Loh T T, Chasteen N D, Bates G W. The exchange of Fe3+ between pyrophosphate and transferrin. Probing the nature of an intermediate complex with stopped flow kinetics, rapid multimixing, and electron paramagnetic resonance spectroscopy. Journal of Biological Chemistry 1986; 261(10):4607-14.] Further, pyrophosphate, in micromolar concentrations, is known to bind tightly to ferric iron, thereby inhibiting its pro-oxidation activity. [Cervato G, Viani P, Cestaro B. Studies on peroxidation processes of model membranes: role of pyrophosphate. Chem Phys Lipids 1990; 56(2-3): 91-9. Cervato G, Viani P, Gatti P, Cazzola R, Cestaro B. Further studies on the antioxidant role of pyrophosphate in model membranes. Chem Phys Lipids 1993; 66(1-2): 87-92.] Neither citrate nor phosphate, for example, exhibits this activity at micromolar concentrations. Compositions of the present invention may contain, by weight, less than about 2% phosphate, less than about 1.5% phosphate, less than about 1% phosphate, or less than about 0.1% phosphate. Higher concentrations of phosphate could increase the risk that water-insoluble phosphate salts will precipitate, either in the solution dosage forms of the composition or in the body following administration. In the body, deposition of phosphate salts in the circulatory system causes endothelial dysfunction. For these reasons, it is expected that pyrophosphate citrate chelate compositions of the present invention will exhibit advantageous biocompatibility as compared to conventional soluble ferric pyrophosphates, ferric salts, ferric polysaccharide complexes, and ferrous salts.

A soluble ferric pyrophosphate citrate chelate composition of the invention can be prepared from stoichiometric portions of a ferric salt, citric acid or a citrate salt, and disodium dihydrogen pyrophosphate or tetrasodium pyrophosphate in a molar ratio of 1:1:0.5 in water. Ferric sulfate, ferric sulfate hydrate, ferric chloride, and ferric ammonium sulfate can be used as the ferric salt (ferric ion source material). Preferably the ferric salt is ferric sulfate hydrate. Citric acid, monosodium citrate, disodium citrate, and trisodium citrate can be used as the citrate (citrate ion source material). Disodium dihydrogen pyrophosphate or tetrasodium pyrophosphate can be used as the pyrophosphate (pyrophosphate ion source material). A suitable reaction temperature is from about 20° C. to about 85° C.

According to a preferred aspect of the present invention, a soluble ferric pyrophosphate citrate chelate composition of the invention can be recovered from a solution of ferric ion, citrate, and pyrophosphate by precipitation. A soluble ferric pyrophosphate citrate chelate composition of the invention may be recovered after a reaction time sufficient to provide a solution of a chelate composition by adding an organic solvent. Suitable organic solvents may be selected from methanol, ethanol, propanol, 2-propanol, acetonitrile, acetone, and 2-butanone.

Advantageously, from an industrial perspective, a process for preparation of solid compositions of a soluble ferric pyrophosphate citrate chelate may employ conventional apparatuses and reagents. Selected process apparatuses may enable control of reaction temperature, monitoring of the progress of reaction for extent of completion, and facilitate removal of impurities.

The ferric pyrophosphate citrate chelate compositions obtained by the methods of the present invention are reproducible and do not contain solvents, chemical contaminants, or biological contaminants. The ferric pyrophosphate citrate chelate compositions of the present invention are easily milled and/or processed into formulary dosage forms using conventional methods and techniques.

The compositions of this invention can be administered by any means that effects contact of the therapeutically active ingredients (i.e., active ingredients) with the site of action in the body of a warm-blooded animal. The active ingredients can be administered by the oral route in solid dosage forms, such as tablets, capsules, powders, chewable compositions, and rapidly dissolving film, or in liquid dosage forms, such as elixirs, syrups, and suspensions. Capsules or tablets for oral administration may contain a controlled-release formulation, and may be provided as a dispersion of active compound in hydroxypropyl methylcellulose or related material known to alter the kinetics of release of the active agent. Solid dosage forms can be manufactured as sustained release products to provide continuous release of medication over a period of hours using known pharmaceutical techniques. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

The active ingredients can be administered by an intravenous route in liquid dosage forms, such as solutions, suspensions, or emulsions.

By way of example, parenteral nutrition (PN), also known as parenteral hyperalimentation, is a medical treatment that supplies nutrition-maintaining compositions intravenously, and is indicated for a variety of mammalian disorders, such as cancer, gastrointestinal diseases, major body burns, extensive wounds, and AIDS. Partial parenteral nutrition supplies only part of daily nutritional requirements, supplementing oral intake. Many hospitalized patients receive dextrose or amino acid solutions by this method. Total parenteral nutrition treatment (TPN) supplies all daily nutritional requirements intravenously, circumventing the gut. TPN may be employed following surgery, when feeding by mouth or using the gut is not possible, when a patient's digestive system cannot absorb nutrients due to chronic disease, or, if nutrition cannot be met by enteral feeding and supplementation. Premature and sick infants often require extended periods of TPN. Compositions for parenteral nutrition typically contain at least water, glucose, amino acids, and optionally emulsified fats. They may be aseptically compounded from amino acid solutions, dextrose solutions, and/or lipid emulsions. PN compositions may further contain vitamins, electrolytes and essential trace elements. The inventors have discovered that a soluble ferric pyrophosphate composition of the present invention is compatible with PN compositions and when admixed with a PN composition provides supplemental iron and pyrophosphate. Supplemental iron and pyrophosphate are useful, by way of example, to treat iron deficiency (anemia) and bone disorders, respectively, in humans and other warm-blooded animals.

Dialysis is a clinical treatment procedure by which metabolic by-products, toxins, and excess fluid are removed from the blood of a subject with chronic kidney disease (CKD) by transfer across a dialysis membrane. Dialysis may be conventionally performed as hemodialysis, in which a synthetic membrane constitutes the dialysis membrane, or as peritoneal dialysis, in which a patient's peritoneal membrane constitutes the dialysis membrane. Dialysis-related iron deficiency affects about 90 percent of CKD patients by six months of treatment, and the inventor expects that a ferric pyrophosphate citrate chelate composition of the invention may be substituted for convention iron fortificants that are administered to CKD patients undergoing dialysis.

In general, the pharmaceutical compositions of this invention can be prepared by conventional techniques, as are described in *Remington's Pharmaceutical Sciences*, a standard reference in this field [Gennaro A R, Ed. *Remington: The Science and Practice of Pharmacy*. 20$^{th}$ Edition. Baltimore: Lippincott, Williams & Williams, 2000]. For therapeutic purposes, the active components of this invention are ordinarily combined with one or more excipients appropriate to the indicated route of administration.

The following examples present useful compositions of the present invention and their anticipated outcomes in treating iron deficits in subjects requiring such treatment. The examples are representative of the scope of the invention, and as such are not to be considered or construed as limiting the invention recited in the appended claims.

EXAMPLE 1

Analysis of samples. The tests and assays listed in Table 3 were used to characterize the soluble ferric pyrophosphate composition of the present invention.

TABLE 3

Tests and assays

| Test | Method | Specification |
|---|---|---|
| Appearance | Visual | Thin, apple-green transparent scales, or pearls, or granules |
| Solubility | Dissolution | 1 gram dissolves slowly but completely in 1 milliliter of water |
| Identification | USP Method for Fe | Responds to the test for ferric iron |
| Identification | USP Method for Phosphorus | Responds to the test for phosphorus (as phosphate) |
| Loss on Drying | USP Method | Dry at 105° C. and report the loss in mass that is observed |
| Iron Assay | Titration | Report results on the dried basis |
| pH of a 5% Solution | USP Method for pH | Report Results |
| Phosphate Assay | Ion-Exchange HPLC with conductivity detection | Report results on the dried basis |
| Citrate Assay | Ion-Exchange HPLC with conductivity detection | Report results on the dried basis |
| Pyrophosphate Assay | | Report results on the dried basis |
| Heavy Metals | Inductively Coupled Plasma Mass Spectrometry | Report Results for each of the following metals in µg/g Aluminum Antimony Arsenic Bismuth Cadmium Copper Lead Mercury Molybdenum Thallium Tin |

EXAMPLE 2

Preparation and precipitation of Soluble Ferric Pyrophosphate: Effects of concentration, cooling, and organic additives. Ferric sulfate (2 g, 2 equiv. iron) was dissolved in 20 mL of water, providing a dark orange solution. A solution of disodium citrate (3.78 g, 4 equiv.) in 30 mL of water and a solution of tetrasodium pyrophosphate (4.8 g, 3 equiv) in 40 mL of water were added dropwise to the ferric sulfate solution. During the addition, the color of the ferric sulfate solution turned from dark orange to light green. When the addition was completed, a clear green solution was obtained. Six milliliter aliquots of the solution were treated as shown in Table 4.

TABLE 4

Evaluation of methods for precipitation of the soluble ferric pyrophosphate composition

| Aliquot No. | Organic Additive | Result |
|---|---|---|
| 1A | None; concentrated under vacuum to a residual gummy solid | Gummy solid |
| 1B | None, solution cooled in ice/alcohol bath | No precipitate |
| 2 | Methanol (2 mL) | Precipitate (Ppt) |
| 3 | Ethanol (0.9 mL) | Ppt |
| 4 | Ethanol (2 mL) | Ppt |
| 5 | Poly(ethylene glycol) (Ave. mol. Wt. 35,000) | Solution remained clear |
| 6 | Acetonitrile (3 mL) | Ppt |
| 7 | Ethanol (3 mL) | Ppt |
| 8 | 2-Propanol (3 mL) | Ppt |

The results indicated that neither concentration nor cooling of the reaction mixture provided the desired product. However, lower alcohols (methanol, ethanol, 2-propanol), and acetonitrile were suitable additives for precipitation of soluble ferric pyrophosphate. Methanol and 2-propanol appeared to provide the most precipitate.

EXAMPLE 3

Preparation and precipitation of Soluble Ferric Pyrophosphate: Effects of changes in solution pH. Ferric sulfate (2 g, 2 equiv. iron) was dissolved in 20 mL of water, providing a dark orange solution having a pH of 1.76. A solution of disodium citrate (3.78 g, 4 equiv.) and tetrasodium pyrophosphate (4.8 g, 3 equiv) in 40 mL of water (and having a pH of 6.31) was added dropwise to the ferric sulfate solution. During the addition, the color of the ferric sulfate solution turned from dark orange to light green. When the addition was completed, a clear green solution having a pH of 5.1 was obtained. Twelve milliliter aliquots were treated as shown in Table 5. Solid sodium bicarbonate was added to adjust the pH of the solution, and then 5 mL of 2-propanol were added to effect precipitation.

TABLE 5

Effects of pH on precipitation

| Aliquot No. | pH Adjustment | Result |
|---|---|---|
| 1 | None | Green Ppt |
| 2 | To pH 6.28 | Green Ppt |
| 3 | To pH 6.43 | Green Ppt |
| 4 | To pH 6.84 | Green-brown Ppt |
| 5 | To pH 7.32 | Brown Ppt |

Although the brown precipitate was soluble in water, it is known that soluble ferric pyrophosphate is green in color. Therefore, adjustment of the pH to more basic values does not provide the desired product.

EXAMPLE 4

Recovery of Conventional Soluble Ferric Pyrophosphate from dissolution/precipitation experiments. Four hundred milligram portions of commercial Soluble Ferric Pyrophosphate were dissolved in a first volume of water. Then a second volume of one of two alcohols, methanol (MeOH) and 2-propanol (IPA), was added. Experimental results are summarized in Table 6.

TABLE 6

Observations from dissolution/reprecipitation experiments

| Expt. No. | Amount of SFP | Solvent System (Ratio by volume) | Observation |
|---|---|---|---|
| 1 | 400 mg | H$_2$O:MeOH (3.5/0.5) | SFP dissolved upon heating; no precipitate (ppt) observed |
| 2 | 400 mg | H$_2$O:MeOH (3/1) | Dissolved upon heating; no ppt observed |
| 3 | 400 mg | H$_2$O:MeOH (1/1) | Would not go into solution, even with heat |
| 4 | 400 mg | H$_2$O:MeOH (2.5/1.5) | Would not go into solution, even with heat |
| 5 | 400 mg | H$_2$O:MeOH (3/1) | Would not go into solution, even with heat |
| 6 | 400 mg | H$_2$O:MeOH (3.5/0.5) | Dissolved upon heating; no ppt observed |
| 7 | 500 mg | H$_2$O:MeOH (3.5/0.5) | Dissolved upon heating; no ppt observed |
| 8 | 600 mg | H$_2$O:MeOH (3.5/0.5) | Dissolved upon heating; no ppt observed |
| 9 | 800 mg | H$_2$O:MeOH (3.5/0.5) | Dissolved upon heating; no ppt observed. Addition of 0.1 mL IPA caused precipitation. |
| 10 | 800 mg | 2 mL H$_2$O, then 1 mL IPA | Solid oiled out after addition of alcohol |
| 11 | 800 mg | 2 mL H$_2$O; then 0.8 mL IPA | Solid oiled out after addition of alcohol. |
| 12 | 800 mg | 2 mL H$_2$O; then 0.1 mL MeOH | Light green solid obtained. Filtered and placed in crystallizing dish to dry. Solid pooled into an oily green substance, and then formed glassy plates on drying at ambient temperature (RT). |
| 13 | 800 mg | 2 mL H$_2$O; then 0.1 mL MeOH | Light green solid. Filtered and placed in crystallizing dish to dry. Solid pooled into an oily green substance, and then formed glassy plates on drying at RT. |
| 14 | 1600 mg | 2 mL H$_2$O; then 0.1 mL MeOH | Light green solid. Filtered and placed in crystallizing dish to dry. Solid pooled into an oily green substance, and then formed glassy plates on drying at RT. |

From these experiments, the following conclusions were drawn. First, the volume of water that is required for dissolution of SFP is small. If too much water is used, the solute may not be easily recovered or is recovered as a hydrate which converts to an oil and/or glassy plates after drying. In subsequent experiments, highly concentrated aqueous solutions were prepared and used. Secondly, IPA appeared to be a better solvent than MeOH for precipitating a solid. However, if too much IPA was used, the light yellow solid which initially formed would oil out and form a very gummy material that was difficult to filter and dry. In contrast, additional MeOH could be used to re-precipitate SFP without causing the "oiling" phenomenon. In subsequent experiments, therefore, MeOH was used as the agent to effect precipitation of SFP.

EXAMPLE 5

Optimization of the molar ratios of reagents. Based on a presumed molecular formula, the molar ratios of reagents shown in Equation 1 were used as a starting point.

$$2Fe_2(SO_4)_3 + 4Na_2C_6H_6O_7 + 3Na_2P_2O_7 \rightarrow SFP \quad (Eq. 1)$$

Uniformly, these experiments yielded a yellow-green powder similar to conventional SFP. However, the yield was highly variable. In addition, the anion composition was different from that of conventional SFP. Data from several experiments are summarized in Table 7. Consistently, products of the invention ("FPCC") contained a much higher percentage of pyrophosphate and a lower percentage of citrate than did conventional SFP. Phosphate was not present in the compositions of the invention unless the wet cake had been dried at 105° C. (first three entries in Table 7). (Sulfate was not monitored.)

TABLE 7

Anion composition of Ferric Pyrophosphate Citrate Chelate Compositions of the invention and conventional SFP

| | Relative Response (Units) | | |
|---|---|---|---|
| Sample ID | Phosphate (Pi) | Citrate | Pyrophosphate (PPi) |
| Conventional SFP-1 | 136.7 | 59.9 | 217.7 |
| Conventional SFP-2 | 155.1 | 58.1 | 230.9 |
| Conventional SFP-3 | 132.6 | 72.2 | 31.8 |
| FPCC-1 | 0 | 51.1 | 567 |
| FPCC-II | 0 | 51.6 | 557.3 |
| FPCC-III | 0 | 50.8 | 552.9 |

EXAMPLE 6

Optimization of the stoichiometric ratios of the starting materials. Experiments were completed to optimize the stoichiometric ratios of the starting materials. The molar ratios of Fe to citrate to pyrophosphate were varied as shown in Table 8. All reactions were run on the same scale relative to the iron source Fe$_2$(SO$_4$)$_3$ (i.e., 1.0 g). All reactions were also run in triplicate at the same concentration in 2.5 mL H$_2$O and precipitated with MeOH (2.5 mL).

TABLE 8

Effects of changes in stoichiometry on product composition

| Experiment Number | Ratio of Fe:Citrate:PPi | Relative Response | | |
|---|---|---|---|---|
| | | Pi | Citrate | PPi |
| 4850-I | 1:2:1 | 0.0 | 75.1 | 249.7 |
| 4850-II | 1:2:1 | 0.0 | 71.4 | 241.8 |
| 4850-III | 1:2:1 | 0.0 | 96.8 | 107.2 |
| 4851-I | 1:1:1 | 0.0 | 42.5 | 261.3 |
| 4851-II | 1:1:1 | 0.0 | 38.7 | 260.4 |
| 4851-III | 1:1:1 | 0.0 | 59.1 | 294.7 |
| 4853-I | 1:1:0.5 | — | — | — |
| 4853-II | 1:1:0.5 | 0.0 | 55.1 | 216.0 |
| 4853-III | 1:1:0.5 | 0.0 | 20.9 | 59.1 |
| 4854-I | 1:0.5:1 | Reaction would not proceed at this ratio. | | |
| 4854-II | 1:0.5:1 | The reactants were not soluble. | | |
| 4854-III | 1:0.5:1 | | | |
| 4858-I | 1:1.25:0.5 | 0.0 | 77.2 | 275.0 |
| 4858-II | 1:1.25:0.5 | 0.0 | 80.8 | 272.5 |
| 4858-III | 1:1.25:0.5 | 0.0 | 81.5 | 273.8 |
| 4859-I | 1:1.5:0.5 | 0.0 | 81.5 | 281.9 |
| 4859-II | 1:1.5:0.5 | 5.9 | 79.7 | 271.5 |
| 4859-III | 1:1.5:0.5 | 0.0 | 72.3 | 221.8 |

The experiments summarized in Table 8 indicated that the most useful ratios of Fe:Citrate:PPi were in the range 1:1:0.5 to 1:1.25:0.5. To confirm this hypothesis and better define the useful ratios for synthesis of SFP, additional experiments were performed (Table 9).

TABLE 9

Experiments designed to define the ratios of reactants

| Sample No. | Ratio of Fe:Citrate:PPi | Weight Percent | | | |
|---|---|---|---|---|---|
| | | Fe | Citrate | Pyrophosphate | Phosphate |
| 4861-I | 1:1:1 | 7.2 | 25.8 | 23.6 | 0 |
| 4861-II | 1:1:1 | 7.8 | 26.7 | 21.2 | 0 |
| 4862-I | 1:1:1 | 6.8 | 22.1 | 19.1 | 0 |
| 4862-II | 1:1:1 | 7.5 | 23.8 | 22.8 | 0 |
| 4862-III | 1:1:1 | 8.0 | 27.8 | 24.9 | 0 |
| 4863-I | 1:1:0.5 | 9.5 | 33.4 | 14.8 | 0 |
| 4863-II | 1:1:0.5 | 9.7 | 33.6 | 15.3 | 0 |
| 4863-III | 1:1:0.5 | 9.1 | 32.4 | 14.3 | 0 |

From these experiments, it was concluded that a molar ratio of at least 1:1 (ferric sulfate to disodium citrate) was suitable. Further, if the molar ratio of pyrophosphate to iron exceeded 0.5:1, the product became increasingly insoluble. With these observations in mind, a molar ratio of ferric sulfate to disodium citrate to tetrasodium pyrophosphate of 1:1:0.5 was selected for use in scale-up experiments.

EXAMPLE 7

Scaled Experiments. The reactions were performed at several scales using standardized conditions (Table 10). A molar ratio of Fe:Citrate:PPi of 1:1:0.5 was used. A solution of disodium citrate and tetrasodium pyrophosphate in water was warmed to about 50° C. Ferric sulfate solid was added, and the reaction mixture was stirred. A dark green solution resulted. The solution was vigorously stirred as methanol was added in a single portion. A lime green precipitate formed, and the reaction mixture was stirred vigorously for several minutes to prevent clumping. The finely divided precipitate was isolated by filtration, air dried, and then dried at 50° C. under vacuum for 3 hr. (Under these drying conditions, no hydrolysis to phosphate was observed.) The material was characterized as shown in Table 10. For reference, conventional SFP was used as a comparator. With the exception of a likely outlier experiment, 4867, the results were reproducible.

TABLE 10

Results of scaled experiments

| Sample ID | Ferric Sulfate, g | Appearance of Product | Weight Percent Composition | | | | Solution (1 g in 10 mL H$_2$O) Dissolution | |
|---|---|---|---|---|---|---|---|---|
| | | | Fe | Citrate | PPi | Pi | Time | pH |
| Conventional SFP | NA | Yellow-green solid | 12.1 | 37.7 | 8.6 | 17.9 | 12 min | 6.49 |
| 4864 | 1 g | Yellow-green solid | 8.6 | 28.1 | 11.8 | 0 | 2.5 min | 3.31 |
| 4865 | 2 g | Yellow-green solid | 8.8 | 37.5 | 12.7 | 0 | 4 min | 3.4 |
| 4866 | 2 g | Yellow-green solid | 10.2 | 32.6 | 13.8 | 0 | 1.5 min | 2.86 |
| 4867 | 5 g | Yellow-green solid | 5.4 | 30.9 | 14.1 | 0 | 4 min | 3.16 |
| 4868 | 10 g | Yellow-green solid | 9.6 | 30.3 | 14.1 | 0 | 4 min | 3.22 |
| 4869 | 10 g | Yellow-green solid | 9.7 | 27.7 | 13.2 | 0 | 4 min | 3.12 |

EXAMPLE 8

Effects of drying temperature. A standard practice in the pharmaceutical industry is drying a material (to constant mass) at 105° C. However, when this practice was implemented, the anion composition of the product changed from [citrate+pyrophosphate] to [citrate+pyrophosphate+phosphate]. A simple experiment was performed to confirm if heating was causing hydrolysis of the pyrophosphate in the product. A reaction was performed under conditions which had previously been observed to give no phosphate. Half of the solid product was dried at ambient temperature and pressure, and the other half was dried at 105° C. The air-dried material was found to have no phosphate, and the oven dried material, as theorized, was found to contain 5.1% phosphate.

EXAMPLE 9

Preparation of Ferric Pyrophosphate Citrate Chelate of the invention: Method A. Sodium hydrogen citrate sesquihydrate ($Na_2C_6H_6O_7.1.5H_2O$; MW 263.11; 0.038 mol; 10.0 g) and tetrasodium pyrophosphate decahydrate ($Na_4P_2O_7.10H_2O$; MW 446.06; 0.019 mol; 8.5 g) were placed in a 250 mL Erlenmeyer flask. After 25 ml of $H_2O$ (5 ml per 2 g ferric sulfate) were added, the reaction mixture was heated with stirring to approximately 50-55° C. The solids dissolved to provide a clear, colorless solution. The reaction mixture was held at about 50° C. for several minutes to ensure complete dissolution.

The reaction mixture was removed from the heat and allowed to cool to room temperature with stirring as $Fe_2(SO_4)_3$ hydrate solid (75.9% $Fe_2(SO_4)_3$; 0.019 mol; 10 g) was added in portions. A clear, dark green solution was thus obtained. The stirring rate was increased to give a vigorously stirred solution, and methanol (70 mL; 14 mL per 2 g ferric sulfate) was added in one portion. A pale green precipitate formed. The supernatant and precipitate were stirred an additional 5 minutes after the addition of the methanol, and then the solid precipitate was isolated by filtration under vacuum. The wet cake was allowed to air dry until drops coming off of the filter tip were about 30 s apart.

The wet cake, a pale yellow-green solid, was transferred to a pre-weighed Pyrex dish and placed in a vacuum oven at 70-75° C. and −760 mmHg. The solid was allowed to dry in the oven for 24 hours, at which time it was removed and allowed to cool to room temperature on the bench top. The cooled solid was then weighed and placed back in the drying oven at 70-75° C. and −760 mmHg. After 2 h the material was removed and allowed to cool to ambient temperature once more and reweighed. The weight did not change. (If additional weight was lost, the dried solid was placed back into the oven at the aforementioned conditions for further drying.) If no further drying was needed, the solid may be ground in a mortar and pestle to give the final powdery material.

Three experiments were performed, and the results given in Table 11 were obtained.

TABLE 11

Results of scaled experiments.

| Lot No. | Yield | Fe | PPi | Citrate | Pi |
|---|---|---|---|---|---|
| 511516 | 17.3 g | 10.83 | 18.3 | 22.4 | 1.3 |
| 511517 | 17.6 g | 10.27 | 17.3 | 23.5 | 1.2 |
| 511913 | 44.0 g (at 25 g scale) | 10.23 | 17.7 | 23.4 | 1.1 |

Weight Percent Composition

EXAMPLE 10

Preparation of Ferric Pyrophosphate Citrate Chelate of the invention: Method B. Trisodium citrate dihydrate ($Na_3C_6H_6O_7.2H_2O$; MW 294.1; 0.038 mol; 11.2 g) and tetrasodium pyrophosphate decahydrate ($Na_4P_2O_7.10H_2O$; MW 446.06; 0.019 mol; 8.5 g) were placed in a 125 mL Erlenmeyer flask. 25 mL of $H_2O$ (5 mL per 2 g ferric sulfate hydrate) were added, and the reaction vessel was placed on a hot plate with good stirring. The temperature was increased to 80-85° C. Once all visible solids were dissolved, the temperature of the clear and colorless solution was held around 80° C. for several minutes to ensure dissolution. The heat source was removed, and stirring was continued.

$Fe_2(SO_4)_3$ hydrate solid (75.9% $Fe_2(SO_4)_3$; 0.019 mol; 10 g) was then added in portions, and the reaction mixture was allowed to cool to room temperature (24° C.). This gave a dark green solution. At this time the stirring rate was increased to give a vigorously stirred solution. Methanol (70 mL) (14 mL per 2 g ferric sulfate) was then added in one portion, and vigorous stirring was continued. A pale green precipitate formed. The precipitate and supernatant were stirred for several minutes after the addition of the methanol. Then the solid was isolated by filtration under vacuum and allowed to air dry until drops coming off of the filter tip were about 30 s apart.

The wet pale yellow-green solid, the desired product, was transferred to a pre-weighed Pyrex dish and placed in a vacuum oven at 70-75° C. and −760 mmHg. The solid was allowed to dry in the oven for 24 hours, at which time it was removed and allowed to cool to room temperature on the bench top. The cooled solid was then weighed and placed back in the drying oven at 70-75° C. and −760 mmHg. After 2 h the material was removed, allowed to cool to ambient temperature once more, and reweighed. If the weight did not change, the dried solid was transferred to amber glass bottles for storage. If a weight change was observed, the material was dried as described above.

Two experiments were performed and the results given in Table 12 were obtained.

TABLE 12

Results of scaled experiments.

| Lot No. | Yield | Fe | PPi | Citrate | Pi |
|---|---|---|---|---|---|
| 512305 | 18.9 g | 8.6 | 15.8 | 22.7 | 1.2 |
| 512426 | 19.0 g | 8.6 | 16.1 | 23.0 | 1.1 |

Weight Percent Composition

EXAMPLE 11

Preparation of Ferric Pyrophosphate Citrate Chelate of the invention: Method C. Citric acid ($C_6H_8O_7$; MW 192.12; 0.01265 mol; 2.43 g), trisodium citrate dihydrate ($Na_3C_6H_6O_7.2H_2O$; MW 294.1; 0.0243 mol; 7.44 g), and tetrasodium pyrophosphate decahydrate ($Na_4P_2O_7.10H_2O$; MW 446.06; 0.019 mol; 8.5 g) were placed in a 250 mL Erlenmeyer flask. After 25 ml of $H_2O$ (5 ml per 2 g ferric sulfate) were added, the reaction mixture was heated with good stirring to approximately 50-55° C. The solids dissolved to provide a clear, colorless solution. The reaction mixture was held at about 50° C. for several minutes to ensure complete dissolution.

The reaction mixture was removed from the heat and allowed to cool to room temperature with good stirring as $Fe_2(SO_4)_3$ hydrate solid (75.9% $Fe_2(SO_4)_3$; 0.019 mol; 10 g) was added in portions. A clear, dark green solution was thus obtained. At this time the stirring rate was increased to give a vigorously stirred solution, and methanol (70 mL; 14 mL per 2 g ferric sulfate) was then added in one portion. A pale green precipitate formed. The reaction was allowed to stir an additional 5 minutes after the addition of the methanol, and then the solid was isolated by filtration under vacuum. The wet cake was allowed to air dry until drops coming off of the filter tip were about 30 s apart.

The wet cake, a pale yellow-green solid, was transferred to a pre-weighed Pyrex dish and placed in a vacuum oven at 70-75° C. and −760 mmHg. The solid was allowed to dry in the oven for 24 hours, at which time it was removed and allowed to cool to room temperature on the bench top. The cooled solid was then weighed and placed back in the drying oven at 70-75° C. and −760 mmHg. After 2 h the material was removed and allowed to cool to ambient temperature once more and reweighed. The weight did not change more than 1%. (The dried solid may be placed back into the oven at the aforementioned conditions for further drying if deemed necessary.)

EXAMPLE 12

Short-term stability of Ferric Pyrophosphate Citrate Chelate of the invention. A 10 g portion of the dried solid was ground and placed in a tared glass dish. The dish was covered with aluminum foil and placed on the bench top. Every 24 hours for 6 successive days, the dish was re-weighed.

EXAMPLE 13

Solubility in water. Weighed portions of a ferric pyrophosphate citrate chelate of the invention were added to 1 mL of water. After each addition, the slurry was stirred and dissolution was monitored. Even after 1 gram of the chelate had been added, the solution was not saturated. Thus, the chelate has a solubility that exceeds 1 gram per milliliter of water and is, by the definition in the U.S. Pharmacopoeia, very water soluble.

EXAMPLE 14

Rate of Dissolution. A 1.0 g portion of each test article was placed in a glass beaker containing a magnetic stirring bar. One hundred (100) mL of aqueous bicarbonate concentrate solution was added to each test article. The slurry was stirred, and the time to complete dissolution was monitored. Experimental data are summarized in Table 13.

TABLE 13

Rate of dissolution

| Sample | Weight | Dissolution Time |
|---|---|---|
| Conventional SFP, micronized | 1.00065 g | 12.48 min |
| Composition of the invention, Lot 511516 | 1.00060 g | 6.25 min |
| Composition of the invention, Lot 512426 | 1.00048 g | 36 sec |

The above description is considered that of the preferred embodiment(s) only. Modifications of the invention will occur to those skilled in the art and to those who make or use the invention. Therefore, it is understood that the embodiment(s) shown in the drawings and described above are merely for illustrative purposes and not intended to limit the scope of the invention, which is defined by the following claims as interpreted according to the principles of patent law, including the doctrine of equivalents.

The invention claimed is:

1. A water-soluble solid ferric pyrophosphate citrate chelate composition comprising:
   iron citrate pyrophosphate; and
   phosphate in an amount of 2% or less by weight.

2. The composition of claim 1, wherein iron is present in an amount of 7% to 11% by weight, citrate is present in an amount of from 14% to 30% by weight, and pyrophosphate is present in an amount of from 10% to 20% by weight.

3. The composition of claim 1, which is soluble in water in an amount of at least 1 gram per milliliter of water.

4. The composition of claim 1, wherein phosphate is present in an amount of 1.5% or less by weight.

5. The composition of claim 1, wherein phosphate is present in an amount of 1% or less by weight.

6. The composition of claim 1, wherein phosphate is present in an amount of 0.1% or less by weight.

7. A process for preparing a water-soluble solid ferric pyrophosphate citrate chelate composition comprising:
   combining a citrate ion source, a pyrophosphate ion source, and a ferric ion source in water to form a solution;
   adding an organic solvent in a volume sufficient to precipitate a solid ferric pyrophosphate citrate chelate composition from the resulting solution; and
   isolating the solid ferric pyrophosphate citrate chelate composition, said chelate composition having 2% or less phosphate by weight.

8. The process of claim 7, wherein the solid ferric pyrophosphate chelate composition has iron present in an amount of 7% to 11% by weight, citrate is present in an amount of from 14% to 30% by weight, and pyrophosphate is present in an amount of from 10% to 20% by weight.

9. The process of claim 7, wherein the amount of citrate ion source, pyrophosphate ion source, and ferric ion source are selected so that the molar ratio of ferric ion:citrate ion:pyrophosphate ion is 0.9 to 1.1:0.9 to 1:1:0.45 to 0.55.

10. The process of claim 7, wherein the amount of citrate ion source, pyrophosphate ion source, and ferric ion source each contain less than 250 micrograms of the metals aluminum, antimony, arsenic, bismuth, cadmium, copper, lead, mercury, molybdenum, thallium, and tin per gram of the ion source.

11. The process of claim 7, wherein the pyrophosphate ion source contains less than 0.1% phosphate.

12. The process of claim 7, wherein the pyrophosphate ion source contains less than 0.01% phosphate.

13. The process of claim 7, wherein the amount of said water used to dissolve the citrate ion source, the pyrophosphate ion source and the ferric ion source is from 1.5 milliliters to 10 milliliters for each gram of ferric ion source.

14. The process of claim 7, wherein said solution is heated to a temperature of from 70° C. to 85° C. before the ferric ion source is added and maintained at a temperature of from 70° C. to 85° C. after the ferric ion source is added and until complete dissolution of the ferric ion source has occurred.

15. The process of claim 14, wherein after the ferric ion source has completely dissolved, the temperature of the solution is lowered to a range of from 15° C. to 75° C. to prevent hydrolysis of pyrophosphate.

16. The process of claim 7, wherein the organic solvent is selected from methanol, ethanol, propanol, 2-propanol, acetonitrile, acetone, 2-butanone, and combinations of these solvents.

17. The process of claim 7, wherein the organic solvent is added to the solution containing the dissolved ferric ion source, the dissolved citrate ion source and the dissolved pyrophosphate ion source in an amount of from 10 to 25 milliliters per gram of the ferric ion source.

18. The process of claim 7, wherein the solid ferric pyrophosphate citrate chelate is dried at a temperature of 80° C. or less.

19. The process of claim 7, wherein the ferric ion source is selected from ferric sulfate, ferric sulfate hydrate, ferric chloride, ferric ammonium sulfate, and combinations of these materials;
   the citrate ion source is selected from citric acid, monosodium citrate, disodium citrate, trisodium citrate, and combinations of these materials; and
   the pyrophosphate ion source is selected from disodium dihydrogen pyrophosphate, tetrasodium pyrophosphate, and a combination of both of these materials.

20. A pharmaceutical composition comprising:
   an oral or parenteral dosage form containing a therapeutically effective amount of a solid ferric pyrophosphate citrate chelate composition having 2% or less phosphate by weight.

21. The composition of claim 20, which is a dialysate.

22. A process for treating iron deficiency comprising:
   administering to a subject in need of treatment for iron deficiency, a pharmaceutical composition comprising an oral or parenteral dosage form containing a therapeutically effective amount of a solid ferric pyrophosphate citrate chelate composition having 2% or less phosphate by weight.

23. The process of claim 22, in which administration is via dialysis.

* * * * *

UNITED STATES PATENT AND TRADEMARK OFFICE
CERTIFICATE OF CORRECTION

PATENT NO. : 7,816,404 B2
APPLICATION NO. : 12/138018
DATED : October 19, 2010
INVENTOR(S) : McCall, Jr.

It is certified that error appears in the above-identified patent and that said Letters Patent is hereby corrected as shown below:

Col. 2, line 17; "L-Ascorbate" should be -- L-ascorbate --.

Col. 4, line 25; "sulphate" should be -- sulfate --.

Col. 5, line 18; "chelae" should be -- chelate --.

Col. 6, line 65; "therapy" should be -- Therapy --.

Col. 10, line 48; "inventors have" should be -- inventor has --.

Col. 10, line 66; "convention" should be -- conventional --.

Col. 13, line 9; "reprecipitation" should be -- precipitation --.

Col. 17, lines 21 and 22;
"$Na_2C_6H_6O_7.1.5H_2O$; . . . $Na_2P_2O_7.10H_2O$" should be
-- $Na_2C_6H_6O_7 \cdot 1.5 H_2O$; . . . $Na_2P_2O_7 \cdot 10 H_2O$ --.

Col. 17, line 24 (2 occurrences); "ml" should be -- mL --.

Col. 18, lines 5 and 6;
"$Na_3C_6H_6O_7.2H_2O$; . . . $Na_4P_2O_7.10H_2O$" should be -- $Na_3C_6H_6O_7 \cdot 2 H_2O$; . . . $Na_4P_2O_7 \cdot 10 H_2O$ --.

Col. 18, lines 59 and 60;
"$Na_3C_6H_6O_7.2H_2O$; . . . $Na_4P_2O_7.10H_2O$" should be -- $Na_3C_6H_6O_7 \cdot 2 H_2O$; . . . $Na_4P_2O_7 \cdot 10 H_2O$ --.

Col. 18, line 62 (2 occurrences); "ml" should be -- mL --.

Col. 20, claim 9, line 38; "are" should be -- is --.

Signed and Sealed this
Twenty-ninth Day of March, 2011

David J. Kappos
*Director of the United States Patent and Trademark Office*

Col. 20, claim 10, line 43; "contain" should be -- contains --.

Col. 22, claim 22, line 11; after "dosage" delete -- from --.